United States Patent [19]

Mannino et al.

[11] Patent Number: 4,871,488

[45] Date of Patent: Oct. 3, 1989

[54] RECONSTITUTING VIRAL GLYCOPROTEINS INTO LARGE PHOSPHOLIPID VESICLES

[75] Inventors: Raphael J. Mannino, Newtonville; Susan G. Fogerite, Waterford, both of N.Y.

[73] Assignee: Albany Medical College of Union University, Albany, N.Y.

[21] Appl. No.: 37,751

[22] Filed: Apr. 13, 1987

Related U.S. Application Data

[62] Division of Ser. No. 725,601, Apr. 22, 1985, Pat. No. 4,663,161.

[51] Int. Cl.[4] .................. A61K 9/64; A61K 37/22; A61K 45/05; B01J 13/02
[52] U.S. Cl. .................................. 264/4.6; 264/4.3; 424/1.1; 424/450; 428/402.2; 436/829; 514/8; 514/885
[58] Field of Search ................. 264/4.6; 428/402.2; 424/89, 450; 514/8, 885; 436/829

[56] References Cited

U.S. PATENT DOCUMENTS

| | | | |
|---|---|---|---|
| 4,148,876 | 4/1979 | Almeida et al. | 424/89 |
| 4,196,191 | 4/1980 | Almeida et al. | 424/89 |
| 4,201,767 | 5/1980 | Fullerton et al. | 424/450 X |
| 4,235,871 | 11/1980 | Papahadjopoulos et al. | 424/92 X |
| 4,261,975 | 4/1981 | Fullerton et al. | 424/450 X |
| 4,356,169 | 10/1982 | Simons et al. | 424/89 |
| 4,416,872 | 11/1983 | Alving et al. | 514/8 |
| 4,551,228 | 11/1985 | Kelly | 426/829 X |
| 4,578,269 | 3/1986 | Morein | 424/89 X |

FOREIGN PATENT DOCUMENTS

| | | | |
|---|---|---|---|
| 2408724 | 9/1974 | Fed. Rep. of Germany | 514/8 |
| 1096951 | 12/1967 | United Kingdom | 424/89 |

OTHER PUBLICATIONS

Scheid et al.: "Identification of Biological, Activities of Paramyxovirus Glycoproteins . . . ", *Virology*, 57, 475-490(1974), [QR1V5].
Papahadjopoulos et al.: "Cochleath Lipid Cylinders: Formation by Fusion of Unilamellar Lipid Vesicles", *Biochimica et Biophysica Acta*, 394 (1975), 483-491, [OD1B5].

*Primary Examiner*—Richard D. Lovering
*Attorney, Agent, or Firm*—Sughrue, Mion, Zinn, Macpeak & Seas

[57] ABSTRACT

The present disclosure relates to novel liposome compositions and methods for their preparation. Utilization of the present invention provides an efficient reconstitution of membrane proteins into large (0.1 to 2 micron diameter) phospholipid vesicles with a large, internal aqueous space. The method has been exemplified with the use of glycoproteins of influenza (A/PR8/34) and Sendai (parainfluenza type I) viruses. The method comprises (A) extracting out the desired membrane protein from a source biological material with an extraction buffer comprising a detergent; (B) mixing the extract with a phospholipid solution and deriving a cochleate intermediate; and (C) forming large phospholipid vesicles with integrated membrane protein in a biologically active state.

6 Claims, No Drawings

RECONSTITUTING VIRAL GLYCOPROTEINS INTO LARGE PHOSPHOLIPID VESICLES

This is a division of application Ser. No. 725,601 filed Apr. 22, 1985, (expected to issue on May 5, 1987) U.S. Pat. No. 4,663,161.

BACKGROUND OF THE INVENTION

Isolation and reconstitution into the bilayer of lipid vesicles or liposomes is one of the most powerful techniques applied to the study of membrane proteins. The simplicity of the resulting model system and the ability to control experimental conditions, allow studies which would be difficult or impossible to perform or interpret using intact cells, viruses, or whole isolated membranes. The structure and function of viral glycoproteins and transport systems, and interactions of membrane receptors with lectins, viruses, and hormones have been investigated using liposome-reconstituted membrane proteins. This approach has also proven useful in a variety of immunological studies involving antibody and complement binding, the activities and generation of cytotoxic T lymphocytes, particle uptake by macrophages and the production of subunit vaccines.

Another reason for reconstituting membrane proteins into artificial lipid bilayers is to modify the properties of liposomes. Liposomes have tremendous potential as delivery vehicles in vivo and in vitro owing to their ability to encapsulate, store, and transport materials. However, they have a low efficiency of attachment to cells. Also, a significant proportion of those which do attach are taken up by endocytosis, which results in their contents being delivered to lysosomes. This is desirable in some cases, as in the proposed treatment of some lysosomal storage diseases by liposomally delivered enzymes. However, if the goal is delivery to the cytoplasm or nucleus in a biologically active form, contact with the lysosomes should be avoided.

In enveloped viruses, the delivery of the viral nucleocapsid to the cytoplasm of the cell in a biologically active form is achieved through the interaction of the viral envelope glycoproteins with plasma membrane components. The viral glycoproteins mediate attachment to cell surface receptors and bring about the fusion of the viral envelope with the cell membrane at the surface, or within the low pH environment of the endocytic vesicle. It has been suggested that liposomes containing these biologically active glycoproteins integrated in their lipid bilayer might be superior delivery vesicles. See in this regard Straubinger et al., Cell 32, 1069 (1983) and Volksy and Loyter, FEBS Lett. 92, 190 (1978). It has been shown that reconstituted Sendai virus envelopes can efficiently deliver entrapped molecules to the cytoplasm and nucleus of animal cells. See in this regard Loyter and Volksy in Membrane Reconstitution, Cell Surface Reviews (Poste, G. and Nicholson, G., eds.) Vol. 8, pp. 216-265 (1982).

The preparation of large unilamellar, phospholipid vesicles made by the use of a calcium-EDTA-chelation technique has been described by Papahadjopoulos et al., Biochim. Biophys. Acta 394, 483 (1978).

However, liposomes prepared in accordance with the teaching of this reference have not been heretofor used to reconstitute membrane proteins in biologically active form. Moreover, the efficiency of encapsulation of materials within the liposome is relatively low.

SUMMARY OF THE INVENTION

The present invention relates to novel liposome compositions and methods for their preparation. Utilization of the present invention provides an efficient reconstitution of membrane proteins into large (0.1 to 2 micron diameter) phospholipid vesicles with a large, internal aqueous space. The method has been exemplified with the use of glycoproteins of influenza (A/PR8/34) and Sendai (parainfluenza type I) viruses. The tight association of the proteins with the lipid bilayer was indicated by their migration with the phospholipid to the top of metrizamide density gradients after sonication, whereas encapsulated FITC-Dextran remained at the bottom of the gradient. Negative staining and electron microscopy showed peplomers on the surface of the vesicles which are indistinguishable from those seen on the respective viruses. The reconstituted membrane proteins have been shown to retain their biological activities of receptor binding and membrane fusion as assayed by their ability to agglutinate and lyse red blood cells. In a preferred aspect, the method of the invention utilizes the nonionic detergent $\beta$-D-octyl-glucopyranoside, which is rapidly and easily removed as the means of extracting the membrane proteins from the viral particles. This procedure does not involve exposure to organic solvents, sonication, or extremes of pH, temperature, or pressure.

In a further preferred aspect of the present invention, the lipid vesicles are formed by use of rotary dialysis of the cochleate intermediates against a calcium chelating agent such as EDTA, EGTA, carbonate, citrate and the like.

DESCRIPTION OF THE INVENTION

In its broadest aspect, the present invention comprises a method for the efficient reconstitution of membrane proteins into large phospholipid vesicles with large, internal aqueous spaces. In the initial step of this method, a desired membrane protein is extracted out from the source particle, cell, tissue, or organism utilizing an extraction buffer containing a detergent which does not destroy the biological activity of the membrane protein. Suitable detergents include ionic detergents such as cholate salts, deoxycholate salts and the like or nonionic detergents such as those containing polyoxyethylene or sugar head groups or heterogeneous polyoxyethylene detergents such as Tween or Brig or Triton. Preferred detergents are nonionic detergents containing sugar head groups such as the alkyl glucosides. A particularly preferred nonionic detergent for this purpose is $\beta$-D-octyl-glucopyranoside. Utilization of this method allows efficient reconstitution of the membrane proteins into the liposomes with retention of biological activities. This step avoids previously utilized organic solvents, sonication, or extremes of pH, temperature, or pressure, all of which may have an adverse effect upon efficient reconstitution in a biologically active form of the desired membrane proteins.

The buffer component utilized in conjunction with the aforesaid detergents can be any conventional buffer employed for membrane protein extractions. A suitable extraction buffer for the present purposes can be prepared utilizing a 2MNaCl, 0.02M sodium phosphate buffer (pH 7.4). The concentration of the detergent component in the buffer is not narrowly critical and can be in the range of from 0.1 to 20% (w/v) preferably from 1 to 5%, most preferably about 2%. The extraction efficiency can be enhanced by utilizing techniques well known in the art, such as by vortexing and sonicating. The extracted membrane proteins can be removed from the remaining nonsoluble debris by procedures well known in the art, such as for example by centrifugation. The resulting supernatant containing the extracted membrane protein may then be applied directly in the liposome formation procedure.

Membrane proteins which can be employed in the practice of the present invention include viral proteins such as for example viral envelope protein, animal cell membrane protein, plant cell membrane protein, bacterial membrane protein, parasite membrane protein, viral membrane protein and the like. These respective proteins can be separated from other components by procedures well known in the art prior to introduction into the present methodology or they can be resolved during the course of the procedure as will be described below.

Suitable viruses which can be employed in conjunction with the method of the invention include Sendai, influenza, herpes simplex or genitalis, HTLV I, II or III, retroviruses, pox virus, respiratory syncytial virus, toga virus, and the like. The present invention can also be employed in conjunction with membrane proteins derived from bacterial or parasitic organisms such as for example organisms causing malaria, chlamydia, N.gonorrhea, salmonella, liver flukes and the like.

The reconstituted viral, bacterial or parasitic membrane proteins in the improved liposome compositions of the present invention can be employed as vaccines to render immunity to hosts treated with such compositions.

In the next step of the method of the present invention, the aforesaid extracted membrane proteins are mixed with phospholipid to form a cochleate intermediate. There are several known procedures for making such cochleates. One such method is the so-called standard cochleate obtained by use of the calcium-EDTA-chelation technique described by Papahadjopoulos et al., supra. In an embodiment of the present invention, a modification of such procedure is employed. In such modified procedure a negatively charged phospholipid such as phosphatidylserine, phosphatidic acid or phosphatidyl glycerol in the absence or presence of cholesterol (up to 3:1, preferably 9:1 w/w) are utilized to produce a suspension of multilamellar protein lipid vesicles which were converted to small unilamellar protein lipid vesicles by sonication under nitrogen. These vesicles are dialyzed at room temperature against buffered calcium chloride resulting in the formation of an insoluble precipitate referred to as a cochleate cylinder. After centrifugation, the resulting pellet can be taken up in buffer to yield the cochleate solution utilized in the preparation of the liposomes of the present invention.

In an alternative and preferred embodiment, an amount of phosphotidylserine and cholesterol in the same proportions as above and equal to from about 1 to 10 times the weight, preferably equal to four times the weight of the viral lipid were utilized to prepare the cochleates. Supernatant from the nonionic detergent extraction of the membrane proteins was then added and the solution vortexed for five minutes. This solution was then dialyzed against buffered calcium chloride to produce a precipitate which can be called a DC (for direct calcium dialysis) cochleate.

An additional, related method for reconstituting membrane proteins into liposomes has been developed. The initial steps involving addition of extracted viral envelope to dried down phosphatidylserine and cholesterol are the same as for the DC method. However, the solution is next dialyzed against Buffer A (with no calcium) to form small liposomes containing the glycoproteins. Calcium is then added either directly or by dialysis to form a precipitate. The precipitate is pelleted and vesicles are formed by direct addition of EDTA or rotary dialysis. These vesicles have physical characteristics and biological activities similar to those formed by the DC method, except that LC's are somewhat smaller and have lower encapsulation efficiencies.

The formation of vesicles from the above intermediates can be carried by alternative methodologies. In one procedure, the aforesaid cochleates were pelleted by centrifugation at 60,000 xg at 5° C. The supernatants were removed and replaced by a small quantity of buffer containing the material to be encapsulated. The pellets were then resuspended by vortexing. Five microliter aliquots of 150 mM EDTA (pH 9.5) are added with gentle mixing and frequent monitoring of pH. It is desired to maintain pH to near neutrality during the vesicle formation procedure. When the pH became slightly basic, 150 mM EDTA (pH 7.5) was added until the cochleates were dissolved and an opalescent suspension of vesicles was obtained.

In an alternative but preferred embodiment, rotary dialysis was employed. In this procedure, the supernatants were removed and transferred to a small segment of dialysis tubing. The dialysis tubing had been previously boiled with a sodium carbonate solution and then with distilled water, cut to the appropriate length and autoclaved in distilled water just prior to use. Small aliquots of buffer (5 to 10 microliters) containing material to be encapsulated were used to rise out the tube and quantitatively tranfer the cochleates to the dialysis bag. The samples were dialyzed by rotating at room temperature against buffered 10 mM EDTA (final pH 7.4) until the cochleate precipitate dissolved and an opalescent suspension of vesicles was obtained.

The methodology employed in the practice of the present invention is more specifically described in the examples which are set forth below.

EXAMPLES

Materials and Methods

Materials. Bovine brain phosphatidylserine in chloroform was purchased from Avanti Polar Lipids, Birmingham, Ala in glass ampules and stored under nitrogen at −20° C. Cholesterol (porcine liver) grade I, n-octyl-$\beta$-D-glucopyranoside, fluorescein isothiocyanate (FITC)-dextran (average mol. wt. 67,000), metrizamide grade I, and chemicals for buffers and protein and phosphate determinations, were obtained from Sigma Chemical Company, St. Louis, Mo. Organic solvents were purchased from Fisher Scientific Co., Fairlawn, NJ. Reagents for polyacrylamide gel electrophoresis were from BioRad Laboratories, Richmond, Ca. S1000 Sephacryl Superfine was obtained from Pharmacia, Piscataway, NJ. Thick walled polycarbonate centrifuge tubes (10 ml capacity) from Beckman Instruments, Palo Alto, Ca, were used for vesicle preparations, washes, and gradients. A bath type sonicator, Model G112SP1G, from Laboratory Supplies Company, Hicksville, NY was used for sonications.

Viral Growth and Purification. Virus was grown and purified essentially as described by Hsu et al., Virology 95, 476 (1979). Sendai (parainfluenza type I) and influenza (A/PR8/34) viruses were propagated in the allantoic sac of 10 or 11 day old embryonated chicken eggs. Eggs were inoculated with 1–100 egg infectious doses ($10^3$ to $10^5$ viral particles as determined by HA titer) in 0.1 ml of phosphate buffered saline (0.2 gm/L KCl, 0.2 gm/L $KH_2PO_4$, 8.0 gm/L NaCL, 1.14 gm/L $Na_2HPO_4$, 0.1 gm/L $CaCl_2$, 0.1 gm/L $MgCl_26H_2O$ (pH 7.2)). Eggs were incubated at 37° C. for 48 to 72 hours, followed by incubation at 4° C. for 24 to 48 hours. Allantoic fluid was collected and clarified at 2,000 rpm for 20 min at 5° C. in a Damon IEC/PR-J centrifuge. The supernatant was then centrifuged at 13,000 rpm for 60 min. This and all subsequent centrifugations were performed in a Sorvall RC2-B centrifuge at 5° C. using a GG rotor. The pellets were resuspended in phosphate buffered saline (pH 7.2) by vortexing and sonicating, followed by centrifugation at 5,000 rpm for 20 min. The pellet was resuspended by vortexing and sonicating, diluted, and centrifuged again at 5,000 rpm for 20 min. The two 5,000 rpm supernatants were combined and centrifuged at 13,000 rpm for 60 min. The resulting pellets were resuspended in phosphate-buffered saline by vortexing and sonicating, aliquoted, and stored at −70° C. Sterile technique and materials were used throughout viral inoculation, isolation, and purification.

Extraction of Viral Glycoproteins and Lipids. Virus stored at −70° C. was thawed, transferred to sterile thick-walled polycarbonate tubes, and diluted with buffer A (2 mM TES, 2 mM L-histidine, 100 mM NaCl (pH 7.4)). It was pelleted at 30,000 rpm for 1 h at 5° C. in a Beckman TY65 rotor. The supernatant was removed and the pellet resuspended to a concentration of 2 mg viral protein per ml of extraction buffer (2M NaCl, 0.02M sodium phosphate buffer (pH 7.4)) by vortexing and sonicating. The nonionic detergent β-D-octylglucopyranoside was then added to a concentration of 2% (w/v). The suspension was mixed, sonicated for 5 sec, and placed in a 37° C. water bath for 45 min. At 15, 30, and 45 min incubation times, the suspension was removed briefly for mixing and sonication. Nucleocapsids were pelleted by centrifugation at 30,000 rpm for 45 min in a TY65 rotor. The resulting clear supernatant was removed and used in the formation of large, viral glycoprotein-containing vesicles. Some modification of the above procedure may have to be employed with other membrane proteins. Such modifications are well known to those skilled in the art.

Formation of Cochleate Intermediates

A. Standard Cochleates.

Large, unilamellar, non-protein-containing, phospholipid vesicles were made by a modification of the calcium-EDTA-chelation technique described by Papahadjopoulos et al Biochim. Biophys. Acta 394, 483 (1975). Phosphatidylserine and cholesterol (9:1 wt ratio) were dried down in a clean glass tube under a stream of nitrogen. The lipid was resuspended in buffer A (pH 7.4) to a concentration of 6 μMol/ml by vortexing for 7 min. The resulting suspension of multilamellar vesicles was converted to small unilamellar vesicles by sonication under nitrogen at 5°–10° C. for approximately 20 min in a bath-type sonicator. (Model G1125P16, Laboratory Supplies Co., Hicksville, NY). These vesicles were dialyzed at room temperature against two changes of 250 ml of buffer A (pH 7.4) with 3 mM $CaCl_2$. This results in the formation of an insoluble precipitate referred to as cochleate cylinders.

B. DC Cochleates.

The envelope glycoproteins of Sendai virus account for about 33% of the total viral protein and are present in approximately equal weight to the viral lipid. An amount of phosphatidylserine and cholesterol (9:1 wt ratio) equal to 4 times the weight of the viral lipid was dried down under nitrogen in a clean glass tube. The amount of lipid added to the influenza virus extract was also equal to four times of the total viral protein. Supernatant from octylglucoside-extracted virus (see Extraction of Viral Lipids and Glycoproteins) was added, and the solution was vortexed for 5 min. This clear, colorless solution was dialyzed overnight at room temperature against two changes of 250 ml buffer A with 3 mM $CaCl_2$. The resultant precipitate has been called DC (for direct calcium dialysis) cochleate.

Formation of Vesicles from Cochleate Intermediates

Cochleates (DC, LC or Standard) were pelleted at 60,000×g at 5° C. for 45 min. If vesicles were to be formed by the direct addition of EDTA, the supernatants were removed and replaced with a small quantity of buffer A containing material to be encapsulated (e.g., 50 μl buffer for 10 mg of phosphatidylserine. The pellets were resuspended by vortexing. Five μl aliquots of 150 mM EDTA (pH 9.5) were added with gentle mixing and frequent monitoring of pH. The use of pH 9.5 EDTA was necessary to maintain near neutral pH during vesicle formation. When the pH became slightly basic, 150 mM EDTA (pH 7.4) was added until the cochleates were dissolved and an opalescent suspension of vesicles was obtained.

In the rotary dialysis method, supernatants were removed, and using a sterile tipped pipetman set at 10 μl, cochleates were transferred to a small segment of dialysis tubing (Spectrapor 4, 6 mm dry diameter). The dialysis tubing had been boiled 2X with a solution of $Na_2CO_3$, then 2X with distilled $H_2O$, cut to the appropriate length, tied at one end, and autoclaved in distilled $H_2O$ just prior to use. Small aliquots of buffer (5 to 10 μl) containing material to be encapsulated were used to rinse out the tube and quantitatively transfer the cochleates to the dialysis bag. The bag was pushed firmly onto the end of a tapered glass rod which had been dipped in 90% alcohol and flamed. Waterproof tape and a Tygon tubing "O" ring were used to further secure the bag to the glass rod. The other end of the rod was inserted in the rotary dialysis apparatus. The samples were dialyzed while rotating overnight at room temperature against buffer A with 10 mM EDTA (final pH 7.4).

Biochemical Characterization of Vesicles

Proteins were determined by the modified Lowry method of Peterson, Analyt. Biochem. 83, 346 (1977). Phospholipid content was calculated from inorganic phosphorous as measured by Bartlett, J. Biol. Chem. 234, 466 (1959). Polyacrylamide gels were run and stained with Coomassie brilliant blue as described by Laemmli, Nature 227, 680 (1970). Alternatively, proteins were visualized using the BioRad silver stain kit. Gels were dried under vacuum between two layers of DuPont film 215 P D cellophane. A Beckman Model R-112 integrating densitometer was used to determine the relative quantities of individual protein bands on polyacrylamide gels.

Electron Microscopic Observations

Samples were negative-stained with 2.5% potassium phosphotungstate (pH 6.7) on carbon supported formvar-coated copper grids, and then examined on a JEOL 100Cx electron microscope.

For freeze fracture, membrane samples were fixed in 2.5% glutaraldehyde in 100 mM cacodylate buffer, pH 7.2, for 2 h at 4° C. and equilibrated with 30% glycerol in cacodylate buffer for 2 h. Samples were quench frozen in Freon 22 cooled with liquid nitrogen and fractured in a Balyers 360M freeze fracture apparatus. Platinum-coated, carbon-supported replicas were examined on a Hitachi HU- 11E electron microscope.

Light Microscopic Observation

Samples were mounted under a glass coverslip, sealed with nail polish, and examined with a Zeiss platoscope III equipped with phase contrast and epifluorescence optics. Photographs were recorded on Kodak Tri-X film that was developed in Diafine.

Results

Structure of the Calcium-Phospholipid Precipitate

In the calcium-EDTA chelation technique of Papahadjopoulos et al. supra., multilamellar vesicles composed of negatively-charged phospholipids are converted into small, unilamellar vesicles by sonication. The addition of calcium to these vesicles causes the formation of a precipitate which, when analyzed by freeze fracture, is shown to consist of jellyroll-like structures called cochleate cylinders. The preferred method of the invention differs in that it uses a high salt buffer, containing detergent-solubilized phospholipid and glycoproteins which is dialyzed against calcium. In the light microscope, the precipitate which forms is seen as numerous spheres approximately one to ten microns in diameter with bumps or spikes on their surfaces, and free phosphatidylserine needles and cholesterol sheets. This is in marked contrast to the fine granular precipitate formed by the calcium-EDTA chelation technique. However, when the precipitate produced in the present method is analyzed by freeze fracture, it is shown to consist of cochleate cylinders.

Qualitative Protein Content of Vesicles

The protein content of vesicles was assessed qualitatively by SDS-polyacrylamide gel electrophoresis. In the case of both Sendai and influenza viruses, the octylglucoside extracted supernatant mainly contains the viral envelope glycoproteins. The influenza virus extract also contains some nucleocapsid protein which co-migrates with the neuraminidase glycoprotein in the gel system. The nucleocapsid protein, however, does not pellet with the cochleate precipitate and is consequently greatly reduced or not present in the reconstituted vesicles.

In addition to the glycoproteins, the Sendai virus octylglucoside extract also contains, as a minor component, a protein which co-migrates with protein 5 of intact virions. Protein 5 has been shown to be related to the nucleocapsid protein. In the above preparations this protein stains much more intensely, relative to the glycoproteins, with silver stain than with Coomassie brilliant blue. The identification of this protein, and information as to why it should be differentially extracted and reconstituted, await further study.

The octylglucoside insoluble pellets contain the other viral proteins. The major components of the influenza pellet are the membrane (M) and nucleocapsid (NP) proteins. The nucleocapsid protein is the major species present in the Sendai virus pellet.

Recovery of Phospholipid and Protein

The quantities of protein present in the octylglucoside extracted supernatants have been consistent with published values for the percent by weight of the virus which is glycoprotein. Small losses of protein and phospholipid result from formation of bubbles at the solubilization step and from transfer losses and dialysis bag adherence at the cochleate formation and rotary dialysis steps. Approximately 70% of the total glycoprotein and phospholipid originally present is associated with the final vesicles. The 6:1 phospholipid/protein ratio of washed, unfractionated vesicles is comparable to that of the starting materials (5:1 ratio).

Density Gradient Fractionation of Vesicles

Vesicles were separated on the basis of density by flotation on discontinuous metrizamide gradients. Under the conditions used, phosphatidylserine:cholesterol vesicles floated to the top fraction and non-vesicle associated protein pelleted. Proteoliposomes were distributed according to their relative protein and phospholipid contents. A heterogeneous population of vesicles, with respect to density, was formed when either rotary dialysis or direct addition of EDTA was used at the vesicle formation stage. The presence of large numbers of vesicles in each fraction was indicated by light scattering, and confirmed by light microscopy and protein and phospholipid determinations.

Because of their lower density, the top and middle fractions contain only vesicle-associated protein. The amount of protein in the bottom fraction, which is vesicle-associated, versus that which is present in protein or protein:phospholipid aggregates cannot be directly determined by this method. It is known that there is a significant population of high density vesicles in the bottom fraction because a substantial percentage of the encapsulated volume on the gradient (measured as fluorescence of FITC-Dextran or radioactivity of $^{14}C$ sucrose in twice washed, pelleted vesicles) is present in the bottom fraction. Also, the phospholipid must be associated with most of the protein present in order for the density to be high enough to keep the vesicles in the bottom fraction.

That these initial gradient positions reflect stable properties of the vesicles can be demonstrated by isolation of individual fractions (top, middle, or bottom) and rebanding of these fractions on separate, identical gradients. Rebanding of vesicles from individual fractions resulted mainly in distribution to the original gradient position, with some redistribution to other fractions..

The Sendai viral glycoproteins are associated with vesicles of all three gradient fractions. The ratio of F to HN varies with the phospholipid:protein ratio and the method of preparation.

Sonication and Rebanding of Vesicles

Flotation of vesicles on metrizamide gradients demonstrated that the viral glycoproteins were vesicle associated. It did not distinguish between protein which was lipid-bilayer integrated, and that which might have been encapsulated within the aqueous interior of the vesicles. Evidence that F and HN were integrated in the lipid bilayer of the vesicles was obtained by the following experiment.

Sendai glycoprotein-containing vesicles and phosphatidylserine:cholesterol vesicles were made by rotary dialysis in the presence of FITC-Dextran. The vesicles were washed twice and then fractionated on metrizamide density gradients. The vesicles floating to the top fraction were isolated and divided into two equal aliquots. One aliquot was sonicated for 5 min in a bath-type sonicator and then refractionated on a second gradient. The other aliquot was rebanded without prior sonication.

Without sonication, the green-yellow FITC-Dextran loaded vesicles mainly redistributed to the top of the gradient. In the sonicated samples, the top vesicle band appeared white, while the bottom of the gradient was a clear, evenly diffused green. From the distribution of fluorescence it was obtained that sonication, which caused these large vesicles to break open and reform as small vesicles, resulted in an almost complete loss of encapsulated material. In contrast, the phospholipid:-protein ratios of the three fractions were largely unaffected, demonstrating that the proteins were tightly associated with the lipid bilayers of the vesicles.

Fractionation of Vesicles by Column Chromatography Using Sephacryl S-1000

The approximate mean size and variation of a population of phospholipid vesicles can be determined by column chromatography using Sephacryl S-1000, see Nozaki et al., Science 217, 366 (1982). This technique was used to evaluate the relative size and polydispersity of the subject vesicles. It was also desired to separate large vesicles from tiny ones and any nonvesicle-associated, aggregated protein which might have been present.

Elution of Sendai viral glycoprotein-containing vesicles, phosphatidylserine:cholesterol vesicles (9:1 weight ratio), and delipidated, aggregated Sendai viral glycoproteins from Sephacryl S-1000 was carried out as follows. A 200 μl sample was applied to a 25.5 cm (height) by 1.1 cm (diameter) column and eluted with Buffer A. Fractions of 1.3 or 0.65 ml were collected, and absorbance at 335 nm (light scattering) or 280 nm (protein absorbance) was determined.

The elution profile of Sendai viral glycoprotein-containing vesicles and influenza vesicles were similar. The vesicles eluted with a fairly sharp front at the void volume, peaking slightly behind it at 8.4 ml eluted volume. The peak broadened with a more gently declining slope in back. The vast majority of the vesicles were eluted by 13.0 ml.

Phosphatidylserine:cholesterol vesicles (9:1 weight ratio) prepared by the calcium-induced fusion technique of Papahadjopoulos et al., supra., exhibited a narrower, more symmetrical profile which peaked at 10.4 ml and was mostly completed at 13.0 ml.

Delipidated Sendai viral glycoprotein aggregates gave a highest point at 15.0 ml. The center, at 8.2 ml, corresponded to the elution peak of bovine serum albumin which was used to determine the included volume of the column. Sendai virus which is 0.1 to 0.2 microns in diameter showed an elution peak at 11.7 ml.

These elution profiles indicated that the glycoprotein-containing vesicles produced by the instant method were heterogenous in size, ranging from 0.1 to several microns in diameter, with most of the population being at the higher end of this range. They also indicated that large, glycoprotein-containing vesicles could be separated from nonvesicle-associated, aggregated protein by elution of Sephacryl S-1000 using these conditions. The protein and phospholipid content of individual fractions, and the fact that the plot of the absorbance at 280 nm paralleled that of light scattering ($OD_{335}$) indicated that the majority of the protein was associated with vesicles.

Morphology of the Vesicles

The morphology of the glycoprotein-containing vesicles was examined by negative staining and electron microscopy. Influenza and Sendai viral glycoprotein-containing vesicles prepared according to the method of the invention using direct addition of EDTA at the vesicle formation step, provided peplomers on the surface of the vesicles which were morphologically indistinguishable from those formed by the glycoproteins integrated in the lipid envelopes of the native virions.

The vesicles were seen to be heterogeneous in size, ranging from 0.1 to 2.0 microns in diameter. These observations correlated well with the data obtained by elution from the Sephacryl S-1000 column.

The arrangement of glycoprotein peplomers on the vesicle surfaces varied from dense, regular packing to sparse, irregular distribution. This variation would give rise to vesicles of different densities, consistent with the studies employing discontinuous metrizamide gradients. There did not appear to be any correlation between vesicle size and protein density; that is, a given peplomer density could be found on vesicles of all sizes.

Biological Activity of Reconstituted Glycoproteins

The HN glycoprotein of Sendai virus and the HA glycoprotein of influenza virus retained their ability to recognize and bind to cellular receptors when reconstituted into vesicles prepared by the method of the invention.

FITC-Dextran was encapsulated within vesicles containing Sendai viral glycoproteins, or phosphatidylserine:cholesterol vesicles. The vesicles were washed twice by dilution and pelleting, followed by fractionation on a discontinuous metrizamide gradient. Vesicles floating to the top fraction were isolated, washed, and mixed on a glass slide with human red blood cells. The slide was rocked for several minutes and the samples were washed by dilution and pelleting to reduce the number of unbound vesicles present. Phase contrast and fluorescent photomicrographs were taken of the same fields for each sample.

Sendai or influenza glycoprotein-containing vesicles which had been separated from nonvesicle-associated protein by Sephacryl S-1000 elution or flotation on metrizamide density gradients showed immediate, massive agglutination of human or chick red blood cells. In contrast, phosphatidylserine:cholesterol vesicles prepared by the calcium-EDTA chelation technique of the art did not cause hemagglutination. FITC-Dextran had been encapsulated within the interior of the vesicles. The same fields, when viewed using fluorescence microscopy, demonstrated that Sendai glycoprotein-containing vesicles had adhered to the surface of the red blood cells, while plain phospholipid vesicles had not. Sendai viral glycoprotein-containing vesicles had also shown hemagglutination titers with human red blood cells which were similar to virus, when compared on a number of particles per milligram of protein basis. They also agglutinated fibroblasts in suspension (mouse L929 and human HeLa) and efficiently associated with fibroblasts in monolayer culture. Similarly prepared phospholipid vesicles exhibited none of these properties.

When red blood cells which had been agglutinated at 4° C. with Sendai viral glycoprotein-containing vesicles were incubated at 37° C., the number and size of the red cell aggregates decreased. This indicated that the neuraminidase activity of the HN glycoprotein (which would cleave the terminal sialic acid from the receptors, liberating the vesicle) was retained on reconstitution.

Hemolysis has been used extensively to demonstrate and investigate the fusogenic activities of viral envelope glycoproteins, see for example Lenard and Miller, Virology 110, 479 (1981). Sendai or influenza viral glycoprotein-containing vesicles prepared by the method of the invention exhibited hemolytic activity. The hemolyzing ability of Sendai virus with that of reconstituted vesicles was compared.

Serial dilutions of virus or vesicles at pH 7.4 were mixed with 0.2 ml of 10% human red blood cells and incubated for 2 h on ice. The samples were transferred to 37° C. Ten hours later the samples were centrifuged at 1000 rpm for 5 min. The supernatants were removed, cleared of vesicles by addition of 100 $\mu$l of 10% SDS, and the optical density at 590 nm was determined.

The Sephacryl S-1000 peak was about one-tenth as active as the virus on a per weight basis. However, relatively small quantities were still able to cause significant hemolysis. The unfractionated vesicles exhibited little activity. This was probably due to the presence of aggregated protein which possessed binding but not significant hemolyzing capability. The retention of the fusogenic activity of the F glycoprotein in these vesicles was also indicated by membrane blebbing and heterokaryon formation by red blood cells and fibroblasts upon incubation with these vesicles at 37$\mu$.

Discussion

A method for the reconstitution of membrane proteins into liposomes has been disclosed. The method has been applied to the reconstitution of the envelope glycoproteins of Sendai and influenza viruses but may also be used with other viruses as well as with membrane proteins from animal, plant, bacterial or parasitic organisms. The tight association with the lipid bilayer, the morphological appearance of the peplomers, and the retention of biological activity, all indicate that the glycoproteins are reconstituted in a manner analoguous to that of the native virion.

The vesicle population which is formed when these viral glycoproteins are reconstituted is heterogeneous with respect to density and size. The vesicles can be fractionated into different density classes by flotation on discontinuous metrizamide gradients.

The Sendai viral glycoproteins are associated with vesicles of all three gradient fractions. The ratio of F to HN varies with the phospholipid:protein ratio and the method of preparation. Rotary dialysis at the vesicle formation step favors a higher proportion of F incorporated into vesicles when compared to vesicle formation by direct addition of EDTA. The ratios of F:HN obtained with rotary dialysis more nearly reflect those of the intact and extracted viral envelope. Lower density vesicles have a higher ratio of F:HN than higher density vesicles when either method of EDTA introduction is employed.

A partial separation according to size can affected by column chromatography using Sephacryl S-1000. Large vesicles which elute at or slightly behind the void volume can be separated from nonvesicle-associated protein which is included. Vesicles eluting toward the front of the peak tend to be larger than those eluting later. The tail of the peak and following fractions contain mostly membrane fragments and aggregates. The hemolytic activity of the vesicles is much more readily demonstrated when the vesicles eluting in the peak are separated from the "interfering" aggregates.

An alternative, related method for reconstituting membrane proteins into liposomes can also be employed. The first step, extraction of the viral envelope and addition to dried down phosphatidylserine and cholesterol, is described in the Materials and Methods section. However, the solution is next dialyzed against Buffer A (with no calcium) to form small liposomes containing the glycoproteins. Calcium is then added either directly or by dialysis to form a precipitate. The precipitate is pelleted and treated as described to form vesicles. These liposomes have biological activity and physical properties similar to the vesicles described above, except that they are somewhat small and have lower encapsulation efficiencies.

The methods of the invention and the resulting protein-lipid vesicles have a number of properties which represent a significant advance in protein reconstitution and liposome production technology. (i) The preferred detergent used is $\beta$-D-octylglucoside. Due to its non-ionic character, functional integrity of the proteins tends to be maintained. Because of its high critical micelle concentration, it can be swiftly and completely removed by dialysis. (ii) The vesicles are large and can efficiently encapsulate large molecules. If smaller vesicles are desired, these can be obtained by extrusion through filters of defined pore size. (iii) A preferred embodiment of the method introduces the technique of rotary dialysis. This facilitates the reconstitution of proteins which have been refractory to other methods. It also increases the efficiency of protein reconstitution and of encapsulation. (iv) The method includes the option of direct addition of EDTA. This allows for the efficient encapsulation of small molecular weight substances which would be lost or diluted during a dialysis step. (v) The method is applicable to the reconstitution of a wide variety of membrane proteins, as well as efficient encapsulation of a large number of substances. A variety of substances, ranging in molecular mass from 342([G-$^{14}$C] sucrose) to $4.5 \times 10^6$ daltons (nick-translated E. coli plasmid pBR322 containing an insert), have been encapsulated at high efficiencies within these vesicles. The presence of a soluble protein at one mg per ml does not interfere with the formation of these vesicles. (vi) These methods do not use organic solvents, sonication, or extremes of temperature, pressure, or pH at points where they might adversely affect the biological activity of components to be encapsulated or reconstituted. (vii) This specific system, using biologically active, reconstituted Sendai or influenza virus glycoproteins can constitute an improved method for delivering molecules, such as nucleic acids, proteins, pharmacologically active agents in a biologically active form to the cytoplasm and the nucleus of animal cells.

We claim:

1. A method for the efficient reconstitution of membrane proteins into large phospholipid vesicles with large internal aqueous spaces, which method comprises in combination:

(A) extracting out the desired membrane protein from a source biological material with an extraction buffer comprising a detergent;

(B) mixing the extract with a negatively charged phospholipid, removing detergent and contacting with a calcium solution to form a cochleate intermediate; and (C) forming large phospholipid vesicles with integrated membrane protein in a biologically active state by contacting a solution of the cochleate intermediate of (B) with a calcium chelating agent, said large phospholipid vesicles being produced by a rotary dialysis procedure against a buffered calcium chelating agent solution as said calcium chelating agent.

2. A method for the efficient reconstitution of a viral glycoprotein into large phospholipid vesicles with large internal aqueous spaces, which method comprises in combination:

(A) extracting out the desired viral glycoprotein from viral particles with an extraction buffer comprising an alkyl glucoside;

(B) mixing the extract with a phospholipid solution and deriving a cochleate intermediate in the form of a precipitate utilizing a direct calcium dialysis procedure; and (C) forming large phospholipid vesicles with integrated viral glycoprotein in a biologically active state by contacting the cochleate intermediate of (B) with an EDTA solution utilizing a rotary dialysis procedure against a buffered EDTA solution.

3. The method of claim 2 wherein said alkyl glucoside is $\beta$-D-octylglucopyranoside.

4. The method of claim 2 wherein said buffered EDTA solution comprises 2 mM TES, 2 mM L-histidine, 100 mM NaCl and 10 mM EDTA (pH 7.4).

5. The method of claim 2 wherein said viral glycoprotein containing phospholipid vesicles are separated from nonvesicle associated protein by a method selected from the group consisting of Sephacryl S-1000 column chromatography and flotation on metrizamide density gradients.

6. A method for the efficient reconstitution of membrane proteins into large phospholipid vesicles with large internal aqueous spaces, which method comprises in combination:

(A) extracting out the desired membrane protein from a source biological material with an extraction buffer comprising a detergent;

(B) mixing the extract with a negatively charged phospholipid, removing detergent and contacting with a calcium solution to form a cochleate intermediate, said cochleate intermediate being derived in the form of a precipitate utilizing a direct calcium dialysis procedure involving removing detergent simultaneously with said contacting with said calcium solution; and (C) forming large phospholipid vesicles with integrated membrane protein in a biologically active state by contacting a solution of the cochleate intermediate of (B) with a calcium chelating solution.

* * * * *